United States Patent [19]

Ahle

[11] 4,008,069
[45] Feb. 15, 1977

[54] SYNERGISTIC WEED CONTROL COMPOSITION
[75] Inventor: James L. Ahle, Shawnee, Kans.
[73] Assignee: Gulf Research & Development Company, Pittsburgh, Pa.
[22] Filed: Sept. 13, 1972
[21] Appl. No.: 288,646
[52] U.S. Cl. .................................... 71/90; 71/118
[51] Int. Cl.² .......................................... A01N 9/22
[58] Field of Search ............................ 71/118, 90; 260/306.8 D Primary Examiner—Lewis Gotts
Assistant Examiner—Catherine L. Mills
Attorney, Agent, or Firm—Carl A. Cline

[57] ABSTRACT

Certain noxious weeds, particularly yellow foxtail (*Setaria glanca*) and beggarweed (*Desmodium torguosum*) are combated in a number of crops by preemergent application of a synergistic combination of preferably about two parts by weight of N-benzyl-N-isopropylpivalamide with one part by weight of 2-cyclopropanecarboxamide-5-(2-chloro-1,1-dimethylethyl)-1,3,4-thiadiazole. Synergistic interaction of the two compounds is graphically illustrated by isobole charts of application rates which produce severe injury to specific weeds.

3 Claims, 1 Drawing Figure

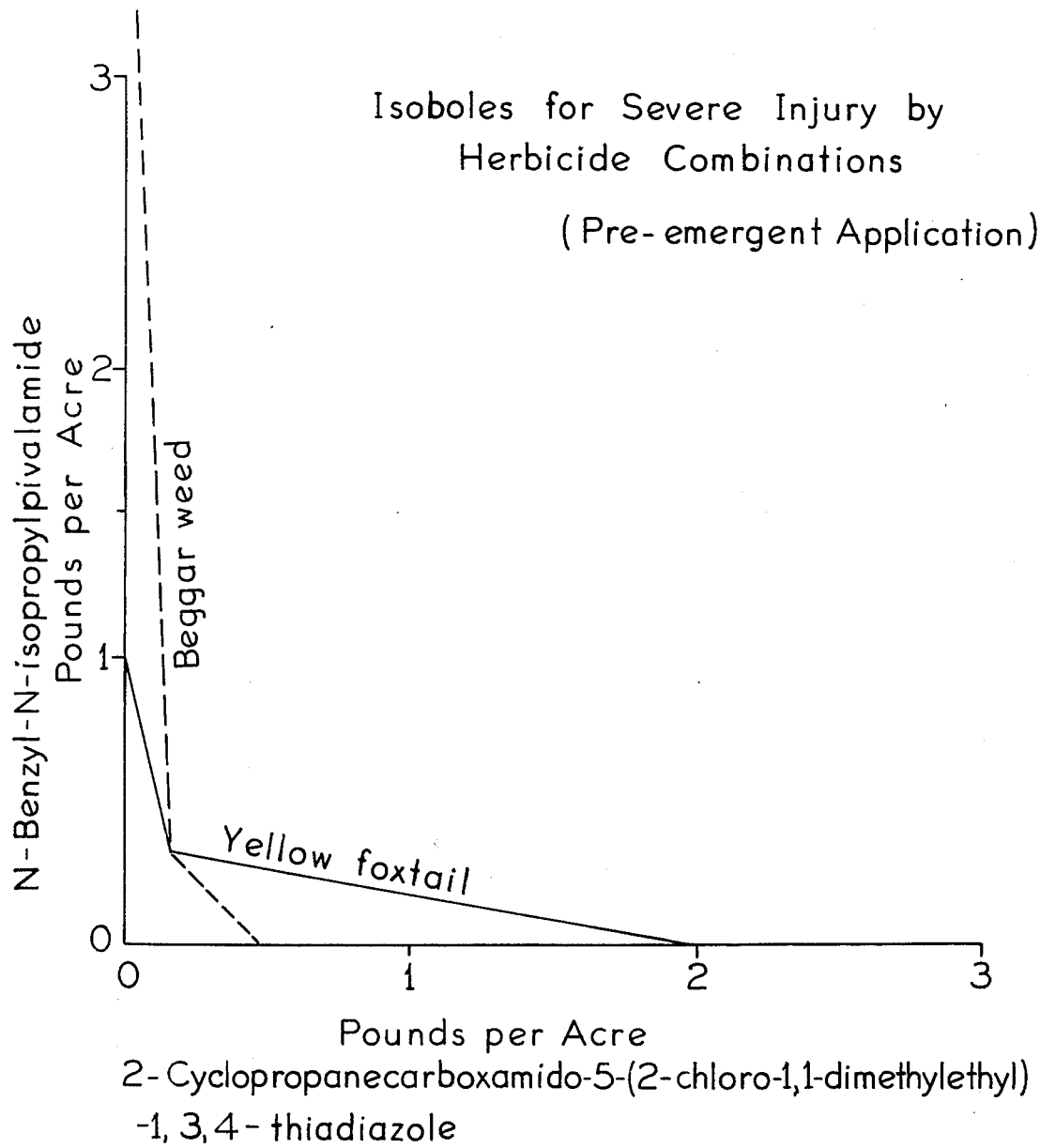

SYNERGISTIC WEED CONTROL COMPOSITION

DESCRIPTION OF THE INVENTION

Yellow foxtail is a common annual noxious grass of very wide distribution in North America, being found as far north as British Columbia and New Brunswick and as far south as Texas and Florida. This plant pest is particularly troublesome during the months of June through September, growing in competition with immature crop plants and causing reduced crop yields. I have discovered that particularly effective control of this noxious annual grass can be obtained by pre-emergent application of an effective amount of a synergistic combination of two herbicides, preferably about two parts by weight of N-benzyl-N-isopropylpivalamide with one part by weight of 2-cyclopropanecarboxamido-5-(2-chloro-1,1-dimethylethyl)-1,3,4-thiadiazole. This combination of herbicides also exhibits a synergistic effect in combating beggarweed, a plant pest which is common in areas where cotton and peanuts are grown. The herbicides employed in the present invention may be made according to methods disclosed, for example in U.S. Pat. No. 3,707,366 of Cahoy and U.S. Pat. No. 3,823,005 of Doyle and Kirkpatrick.

The following discussion is presented in an effort to review present knowledge of the nature of synergism and explain the manner in which evidence of synergism is present herein.

HERBICIDE INTERACTION

In the use of herbicides or other pesticides it is seldom that one specific pesticide does everything that the user desires to accomplish. In an effort to obtain the best of all possible characteristics possessed by two or more pesticides it has become common practice to use these substances in various combinations. The results obtained by the use of combinations of herbicides are usually about what would be expected if one considers carefully the nature of the selectivity patterns of the individual chemicals in a combination. Selectivity is normally a relative, not an absolute characteristic. A chemical is often safe to use on a particular crop because the minimum effective dose for crop injury barely exceeds the minimum dose for complete control of the weeds. Unfortunately the borderline toxicities in the selectivity patterns of individual herbicides often add together when herbicides are combined, so that the combination is no longer safe on as many crop species as any one of the herbicides taken alone. Herbicide combinations are therefore usually recommended for use in only one or two crops. This type of result might be classified as a neutral one, indicating no particular effect of any herbicide on another.

Occasionally there is evidence of antagonism by the specific herbicides in a combination, which manifests itself in an unexpected failure to control some specific weed. More rarely, a combination of herbicides possesses such effectiveness against some undesirable plant species that the result cannot be explained on the basis of known phytotoxicity of the individual components of the combinations. These unexpected increases in effectiveness of chemical agents have been observed, for example, in herbicides, insecticides and chemotherapeutic agents. Probably because these effects defy all attempts at explanation, the term "synergism" has been employed to describe the phenomenon. Presumably this term was selected because it originally was used to identify the ancient theological doctrine or belief that there is a cooperation of divine grace with human activity. Thus, since we can find no other reason for the unexpected beneficial results, they are attributed to the influence of divine assistance.

Although there is no precise definition of "synergism", a "synergist" is defined clearly as an agent that increases the effectiveness of another agent when combined with it. This definition includes both active pesticides and substances which have no effectiveness at all, if they interact with pesticides to improve effectiveness.

In the case of combinations of herbicides, the term "synergism" is now used generally to indicate a response in excess of that expected from the sum of the effects of various chemicals when used separately under the same conditions. There are various ways of interpreting data so as to identify and estimate the extent of synergism.

In order to determine whether or not an unexpected interaction of two or more herbicides has occurred it is necessary first of all to decide just what constitutes expected behavior. The determination of the expected effect is difficult and can only occasionally be established by simple summation of numerical scores of the responses obtained with each chemical used separately. In a combination of herbicides, when one chemical has already killed a number of individual plants, the other chemical may appear to be either more or less effective than when used individually, depending upon various factors, including the level of effectiveness which is arbitrarily selected for comparison purposes and on the degree to which susceptibility to the two toxicants is related. If the two toxicants affect the plant by different biochemical mechanisms, the evidence of synergism may be dramatically apparent. However, if both toxicants operate by the same mechanism, the evidence of synergism may be erratic, only becoming clearly apparent when both toxicants are employed at application rates substantially above the level of minimum observable effect (threshhold). The occurrence of different threshhold application rates below which toxicants are ineffective, or in other words, the variation of regression of response to dose of individual herbicides, makes it extremely difficult to determine precisely what herbicidal response would be reasonably expected from a herbicide combination. This problem has been given considerable attention by research workers in this field and various methods of obtaining and treating data have been proposed.

Graphical methods of treating data include the plotting of percentage of plant growth response (measured by weight of new growth) versus herbicide application rate, percentage response versus logarithm of herbicide application rate and the reciprocals of percentage response versus reciprocals of herbicide application rate. Herbicide antagonism or synergism is indicated by differences in slope of straight line plots and in differences in shape of curves. (Gowing, D. P. 1960. Comments on Tests of Herbicide Mixtures. *Weeds* 8: 379–391.)

Efforts have been made to place numerical values on synergistic and antagonistic effects in herbicide combinations. For example, the expected response for a combination of herbicides may be determined by taking the product of the percent-of-control values for individual herbicides applied alone and dividing by $(100)^{n-1}$ where $n$ is the number of herbicides in the combination.

(Colby, S. R. 1967. Calculating synergistic and antagonistic responses of herbicide combinations. *Weed* 15: 20–22.)

Another approach to evaluation of interaction of herbicides has been to average the herbicide control scores on a number of plant species, both for combinations and for the individual herbicides. An increase in the average rating of a combination over the average ratings for the same total amount of either pesticide applied alone has been considered to indicate a synergistic effect. A strange thing about the use of the averaging approach is that an increase in average control may be observed while at the same time no additional species is controlled effectively. The increase in average ratings may occur entirely as a result of a general increase in apparent toxicity, resulting from the additive overlapping of borderline toxicity in the selectivity patterns, as discussed above. (See, for example, U.S. Pat. No. 3,535,102.)

In other efforts to put a quantitative value on cotoxicity results, the concept of the cotoxicity coefficient has been employed. (The method of Yen-Pei Sun and E. R. Johnson, *Journal of Economic Entomology*, vol. 53, 887–892.) In general, all mathematical methods of treating data on herbicide interaction suffer from the low level of mathematical significance in the data.

Another concept which has been employed is a graphic one in which the rate of application of one pesticide in a combination versus the rate of application of another pesticide in the combination is plotted for one specific level of effectiveness, for example, 50% control or inhibition of growth on one plant species. If there is no interaction of the two pesticides the graph should theoretically be a straight line. These graphs, called "isoboles", sometimes show both synergism and antagonism within certain ranges of composition and may indicate both interaction and non-interaction of the two pesticides at various ratios of components in the pesticide combination. (Colby, S. R. and R. W. Feeney, 1967. Herbicidal Interactions of Potassium Azide with Calcium Cyanamid. *Weeds* 15(2): 163–167, also Tammes, P. M. L. 1964. Isoboles, a Graphic Representation of Synergism in Pesticides. *Neth. J. Plant. Path.* 70: 73–80.)

Synergism in combinations of herbicides may be only of academic interest and have no relation to utility unless it occurs at or near the application rates which can be employed to control weeds in the field. Synergism can be particularly valuable when it occurs at concentration levels slightly below those obtained by application in the field. As concentration on the plants declines during the days after application, the synergistic effect will sustain the effectiveness of the herbicide combination for a longer period of time than normally expected, resulting in the killing of many severely injured weeds which might otherwise recover and produce seed in the field. The plotting of isoboles for combinations of two herbicides at the level of severe injury, at which only a few of the test plants fail to die, therefore reveals herbicide interactions of special significance with respect to utility.

The use of the herbicides both individually and in synergistic combination so as to obtain reliable measures of herbicidal effects may be performed according to the procedures discussed below.

USE OF THE HERBICIDES

There are described below illustrative procedures for use of the herbicidal compounds under controlled conditions in the greenhouse, so as to obtain data on phytotoxic activity and selectivity.

1. Post-Emergent Use (Initial Tests)

An aqueous dispersion of each active compound is prepared by combining 0.4 gram of the compound with about 4 ml of a solvent-emulsifier mixture (3 parts of a commercial polyoxyethylated vegetable oil emulsifier, one part xylene, one part kerosene) and then adding water, with stirring, to a final volume of 40 ml.

The species of plants on which each compound is to be tested are planted in 4-inch pots in a greenhouse. Ten to fourteen days after emergence of the plants, one pot of each species is sprayed with an aqueous dispersion of the active compound prepared as described above, at a rate of 5 lb of active compound per acre and at a spray volume of 60 gallons per acre. Approximately 12 days after the spray application the plants are observed and the results rated.

Pre-emergent herbicidal test results may be obtained according to the procedure described below.

2. Pre-Emergent Use (Initial Tests)

A solution of each active compound is prepared by dissolving 104 mg of the compound to be tested in 100 ml of acetone. Disposable expanded polystyrene trays about 2 ½ inches deep and about one square foot in area are prepared, seeded and sprayed with the acetone solution at the rate of 10 lb of active chemical per acre of sprayed area and are then covered with about ¼ inch of soil. One group of trays, which have been seeded with alfalfa, brome, flax, oats, radishes and sugar beets is held at 75° F day temperature; another set of trays seeded with corn, coxcomb, cotton, crabgrass, millet and soybeans is held at 85° F. 21 days after seeding and treatment the plantings are examined and herbicidal effects are rated according to the schedule as described in the following discussion.

THE RATING OF HERBICIDE TEST RESULTS

So as to assure that the numerical data from greenhouse tests are significant, the scores of the observations recorded herein are limited to only 5 specific ratings which are judgments made as discussed below:

0 (No Effect)

This rating, as with all the other ratings, is determined by comparison with test plants grown under identical conditions but without treatment with herbicides. If no difference between the untreated plants and herbicide-treated plants is observable, the rating is 0.

1 (Slight Effect)

If there is stunting, slight difference in color, a few dead leaves or other effect which is definitely different from the check plants but from which the plants appear to have recovered, the rating is 1. It is true that the plants may prove to be a bit retarded and may flower or mature a little later than the check plants if retained in the greenhouse, but experience has shown that plants given this rating are otherwise normal. The rating indicates only a difference in appearance which shows that a temporary effect has occurred.

2 (Moderate Effect)

Plants which exhibit substantial permanent injury of various sorts, but in which all individuals are still alive are given a rating of 2. Only a few species merit holding in the greenhouse for another 2 or 3 weeks to determine whether this rating is accurte. Occasionally on some plant species the condition of new growth shows increasing indication of injury during the last 2 or 3 days of the test. These plants may be held for further observation to see if the rating must be changed to 3.

3 (Severe Effect)

When injury is readily apparent and most, but not all plants are dead in every pot, the rating is 3. Occasionally these pots are held for a further length of time to determine if the other plants are dying. If all of them are, the rating is changed to 4.

4 (Complete Control)

When all the plants in one set of pots die, the rating is 4. This rating is reliable and usually repeatable, but is less significant than a rating of 3 from the scientific standpoint. There are no distinctions between dead plants; therefore some may have received only sufficient herbicide, while others may have been subject to much more than the lethal dose. Ratings of 4, however, are the ones in which the people concerned with commercial weed control are interested. They avoid using a treatment which yields a rating of 3 because it may result in loss of crop yield and may lead to development of herbicide-resistant strains of weeds.

SOURCES OF VARIATIONS IN GREENHOUSE TEST RESULTS

Quantitative results obtained from working with living plants are always subject to some variations, the principal sources of which are discussed below.

1. Duration and Intensity of Sunlight

A definite variation in test results is observed when experiments conducted in cloudy weather are compared with those performed in periods of intense sunlight. In general, cloudy weather appears to have the effect of weakening of the plants so that herbicide ratings are a little higher. There are also some unexplained variations in test results with the season of the year which may be attributable to differences in intensity, duration and angle of incidence of sunlight.

2. The Nature of Individual Seeds

This is a troublesome, uncontrollable experimental variable. Weed seeds are not as uniform as crop seeds, regardless of the source of supply. Weeds are notoriously variable in genetic make-up, having such a great variety of heredity among individual plants that within only a few generations of survivors they easily establish weed populations which resist adverse conditions of climate, soils, shading, herbicides and so forth.

3. Temperature

In mid-summer, excessively high temperatures may occur in greenhouses in the temperate climate zones in spite of best efforts to keep the temperature under control. Tests are customarily suspended during extremely hot weather, during which time greenhouses may be shut down for cleaning and maintenance. During the rest of the year, temperatures may be kept substantially constant during testing and this is therefore not a serious source of error.

4. Changing Length of Days

Although the overall intensity and distribution of wavelengths of natural sunlight cannot, in the present state of the art, be duplicated exactly by artificial light, the length of days may be regulated to a constant value by means of artificial lights of a modern type which are manufactured and sold for this purpose. The triggering of flowering, dormancy and other behavior of plants in response to changing length of days is in this way substantially eliminated as source of error.

5. Variation in Stage of Growth of Test Plants

As plants grow and develop, there are significant differences in sensitivity to herbicides at different stages of growth. When tests are made at different times, with different plants, results are not strictly comparable unless the test plants are sprayed at precisely the same stage of growth. In general, larger, more mature plants are more resistant to post-emergent herbicides than are younger plants. Since stage of growth of weeds is only one of many uncontrolled variables in the use of herbicides outdoors in fields of growing crops, the results obtained in the field are generally less reproducible than results of greenhouse tests.

SELECTION OF PLANT SPECIES FOR GREENHOUSE TESTING

Plants selected from the following species may conveniently be employed in initial pre-emergent herbicide tests, so as to obtain evidence of phytotoxicity to a variety of dissimilar plant species.

| COMMON NAME | SCIENTIFIC NAME |
| --- | --- |
| Crabgrass | Digitaria sanguinalis |
| Brome | Bromus inermis |
| Sugar beet | Beta vulgaris |
| Cockscomb | Celosia plumosa |
| German millet | Setaria italica |
| Radish | Raphanus sativus |

The following dissimilar plant species may also be employed in initial post-emergent herbicide tests:

| COMMON NAME | SCIENTIFIC NAME |
| --- | --- |
| Tomato | Lycospersicum esculentum |
| Sugar beet | Beta vulgaris |
| Alfalfa | Medicago sativa |
| Oats | Avena sativa |
| German millet | Setaria italica |
| Radish | Raphanus sativus |

In further greenhouse tests to define the selectivity patterns and indicate extent of utility of herbicides, the following dissimilar species may be conveniently employed:

| COMMON NAME | SCIENTIFIC NAME |
| --- | --- |
| Pigweed | Amaranthus retroflexus |
| Lambsquarters | Chenopodium album |
| Wild buckwheat | Polygonum convolvulus |
| Wild mustard | Brassica kaber |
| Cocklebur | Xanthium pensylvanicum |
| Morning glory | Ipomoea purpurea |
| Crabgrass | Digitaria sanguinalis |
| Downy brome | Bromus tectorum |
| Giant foxtail | Setaria faberii |
| Barnyard grass | Echinochloa crusgalli |
| Green foxtail | Setaria viridis |
| Wild cane | Sorghum bicolor |
| Wild oats | Avena fatua |
| Yellow nutsedge | Cyperus esculentus |
| Cotton | Gossypium herbaceum |
| Peanuts | Arachis hypogaea |
| Tomato | Lycospersicum esculentum |
| Sugar beets | Beta vulgaris |
| Soybean | Soja max |
| Alfalfa | Medicago sativa |
| Corn | Zea mays |
| Grain sorghum | Sorghum vulgare |
| Wheat | Triticum aestivum |

-continued

| COMMON NAME | SCIENTIFIC NAME |
|---|---|
| Rice | Oryza-sativa |

So as to further evaluate characteristics of herbicides with respect to crop injury, tests may be made on various crop species, for example, species selected from the following list:

| COMMON NAME | SCIENTIFIC NAME |
|---|---|
| Sugar cane | Saccharum officinarum |
| Sweet corn | Zea mays |
| Pop corn | Zea mays |
| Perennial ryegrass | Lolium perenne |
| Kentucky bluegrass | Poa pratense |
| Kentucky 31 fescue | Festuca elatior |
| Wheat | Triticum aestivum |
| Barley | Hordeum vulgare |
| Rye | Secale cereale |
| Sudan grass | Sorghum vulgare |
| Atlas sorgo | Sorghum vulgare |
| Creeping red fescue | Festuca rubra |
| Onion | Allium cepa |
| Buckwheat | Fagopyrum sagittalum |
| Table beets | Beta vulgaris |
| Spinach | Spinocia oleracea |
| Cabbage | Brassica oleracea |
| Rape | Brassica napus |
| Turnip | Brassica rapa |
| Strawberry | Fragaria sp. |
| Bush bean | Phaseolus vulgaris |
| Lima bean | Phaseolus limensis |
| White clover | Trifolium repens |
| Peas | Pisum sativum |
| Red clover | Trifolium pratense |
| Flax | Linum usitatissimum |
| Carrot | Caucus carota |
| Sweet peppers | Capsicum grossum |
| Potato | Solamum tuberosum |
| Tobacco | Nicotiana tobacum |
| Cantaloupe | Cucumis melo |
| Cucumber | Cucumis sativus |
| Squash | Cucurbita maxima |
| Watermelon | Citrullus vulgaris |
| Lettuce | Lactuca sativa |
| Safflower | Carthanus tinctorius |

To further evaluate the utility of a herbicide in weed control, tests may be made on species of weeds selected from the following list:

| COMMON NAME | SCIENTIFIC NAME |
|---|---|
| Fall panicum | Panicum dichotomiflorum |
| Yellow foxtail | Setaria glauca |
| Cheat | Bromus secalinus |
| Raoul grass | Rottboellia exultata |
| Quackgrass | Agropyron repens |
| Johnson grass | Sorghum halepense |
| Sesbania | Sesbania exaltata |
| Sicklepod | Cassia obtusifolia |
| Beggarweed | Desmodium tortuosum |
| Velvetleaf | Abutilon theophrasti |
| Kochia | Kochia scoparia |
| Purslane | Portulaca oleracea |
| Black nightshade | solanum nigrum |
| Jimsonweed | Datura stramonium |
| Sunflower | Helianthus annuus |
| Ragweed | Ambrosia sp. |
| Dodder | Cuscuta sp. |
| Florida pusley | Richardia scabra |
| Smartweed | Polygonum pennsylvanicum |
| Common chickweed | Stellaria media |
| Prickly sida | Sida spinosa |
| White cockle | Lychnis alba |
| Dandelion | Taraxacum officinale |
| Buckhorn plantain | Plantago lanceolata |
| AQUATIC WEEDS | |
| Cabomba | Cabomba caroliniana |
| Salvinia | Salvinia rotundifolia |
| Duckweed | Lemma minor |
| Azolla | Azolla caroliniana |
| Elodea | Hydrilla verticillata |
| Watermilfoil | Myriophyllum specatum |

By means of pre-emergent application according to procedures disclosed above, N-benzyl-N-isopropyl-pivalamide and 2-cyclopropanecarboxamide-5-(2-chloro-1,1-dimethylethyl)-1,3,4-thiadiazole have been evaluated for effects, both individually and in combination against yellow foxtail, beggarweed and several other species of plants. The scores, obtained by rating the results in the manner discussed above, are tabulated below. Isobole charts for the two herbicides at the level of severe injury for both beggarweed and yellow foxtail appear in the drawing. The synergistic effect on both weeds of an effective amount of the preferred combination is readily apparent.

RESULTS OF PRE-EMERGENT APPLICATION OF HERBICIDES

| Application Rate Pounds per Acre | | PLANT SPECIES | | | | | | | | | | | | |
|---|---|---|---|---|---|---|---|---|---|---|---|---|---|---|
| N-Benzyl-N-isopropyl-pivalamide | 2-Cyclo-propane-carbox-amido-5-(2-chloro-1,1-dimethyl-ethyl)-1,3,4-thiadiazole | Beggar-weed | Yellow Foxtail | Velvet Leaf | Crab-grass | Sickle-pod | Cot-ton | Pea-nuts | Pig-weed | Jimson weed | Smart-weed | Cockle bur | Soy bean | Morn-ing glory |
| 4 | 0 | 2 | 4 | 0 | 4 | 0 | 0 | 0 | 3 | 4 | 4 | 0 | 0 | 0 |
| 2 | 0 | 1 | 4 | | | | | | | | | | | |
| 1 | 0 | 0 | 3 | 0 | 4 | 0 | 0 | 0 | 1 | 0 | 3 | 0 | 0 | 0 |
| 1/2 | 0 | 0 | 2 | 0 | 3 | 0 | 0 | 0 | 0 | 0 | 2 | 0 | 0 | 0 |
| 1/4 | 0 | 0 | 1 | | | | | | | | | | | |
| 0 | 4 | 4 | 4 | | | | | | | | | | | |
| 0 | 2 | 4 | 3 | 4 | 4 | 4 | 4 | 1 | 4 | 4 | 4 | 4 | 4 | 4 |
| 0 | 1 | 4 | 0 | 3 | 1 | 4 | 1 | 0 | 4 | 4 | 4 | 4 | 4 | 4 |
| 0 | 1/2 | 3 | 0 | 2 | 0 | 2 | 0 | 0 | 3 | 2 | 4 | 0 | 2 | 2 |
| 0 | 1/4 | 1 | 0 | | | | | | | | | | | |
| 2 | 2 | 4 | 4 | | | | | | | | | | | |
| 2 2/3 | 1 1/3 | 4 | 4 | | | | | | | | | | | |
| 1 | 1 | 4 | 4 | | | | | | | | | | | |
| 1 1/3 | 2/3 | 4 | 4 | 3 | 4 | 3 | 1 | 0 | 4 | 3 | 4 | 2 | 2 | 4 |
| 1/2 | 1/2 | 4 | 4 | | | | | | | | | | | |
| 2/3 | 1/3 | 4 | 4 | 0 | 4 | 3 | 0 | 0 | 4 | 1 | 4 | 0 | 0 | 1 |
| 1/4 | 1/4 | 4 | 2 | | | | | | | | | | | |
| 1/3 | 1/6 | 4 | 3 | 0 | 3 | 1 | 0 | 0 | 2 | 0 | 2 | 0 | 0 | 0 |

-continued

RESULTS OF PRE-EMERGENT APPLICATION OF HERBICIDES

| Application Rate Pounds per Acre | | PLANT SPECIES | | | | | | | | | | | | |
|---|---|---|---|---|---|---|---|---|---|---|---|---|---|---|
| N-Benzyl-N-isopropyl-pivalamide | 2-Cyclopropane-carboxamido-5-(2-chloro-1,1-dimethyl-ethyl)-1,3,4-thiadiazole | Beggar-weed | Yellow Foxtail | Velvet Leaf | Crab-grass | Sickle-pod | Cot-ton | Pea-nuts | Pig-weed | Jimson weed | Smart-weed | Cockle bur | Soy bean | Morning glory |
| 1/8 | 1/8 | I | I | | | | | | | | | | | |
| 1/6 | 1/12 | I | I | | | | | | | | | | | |

I claim:

1. The synergistic pre-emergent weed control composition consisting essentially of a herbicidally effective amount of a mixture of one part by weight 2-cyclopropanecarboxamido-5-(2-chloro-1,1-dimethylethyl)-1,3,4-thiadiazole and two parts by weight N-benzyl-N-isopropylpivalamide.

2. The method of combating beggarweed consisting of applying pre-emergently to the locus of the weed seeds an effective amount of a combination of one part by weight of 2-cyclopropanecarboxamido-5-(2-chloro-1,1-dimethylethyl)-1,3,4-thiadiazole and approximately two parts by weight of N-benzyl-N-isopropylpivalamide.

3. The method of combating yellow foxtail consisting of applying pre-emergently to the locus of the weed seeds an effective amount of a combination of one part by weight of 2-cyclopropanecarboxamido-5-(2-chloro-1,1-dimethylethyl)-1,3,4-thiadiazole and approximately two parts by weight of N-benzyl-N-isopropylpivalamide.

* * * * *